United States Patent [19]

Happle et al.

[11] Patent Number: 4,985,464
[45] Date of Patent: Jan. 15, 1991

[54] DRUG COMPOSITIONS FOR LOCAL TREATMENT OF ALOPECIA AREATA

[76] Inventors: Rudolf Happle, Schildstiege 2, D-4400 Münster; Bjorn Hausen, Wilhelmstrasse 4, D-2082 Tornesch, both of Fed. Rep. of Germany

[21] Appl. No.: 693,850

[22] Filed: Jan. 22, 1985

Related U.S. Application Data

[63] Continuation of Ser. No. 613,253, May 23, 1984, abandoned, which is a continuation of Ser. No. 362,474, Mar. 26, 1982, abandoned.

[51] Int. Cl.$^5$ .............................................. A61K 31/12
[52] U.S. Cl. .................................... 514/679; 514/676; 514/678; 514/682; 514/880; 514/881
[58] Field of Search ............... 514/880, 881, 676, 678, 514/679, 682, 657

[56] References Cited

U.S. PATENT DOCUMENTS 3,366,664  1/1968  Andreades .
3,657,348  8/1972  Tobey .
3,787,500  1/1974  Tobey .

OTHER PUBLICATIONS

*Current Therapy*, pp. 599–603, (1984).
*Current Therapy*, pp. 679–680, 755–757, 662, (1981).
Happel, et al., *Acta Dermatovener* (Stockholm) 63: 49–52, 1983, *Deiphencyprone in the Treatment of Alopecia Areata*.
Wilkerson, et al., *L. Amer. Acad. Dermatol.* 11: 802–807, (Nov. 1984), Diphenylcyclopropenone: Examination for Potential Contaminants, Mechanism of Sensitization, and Photochemical Stability.

*Primary Examiner*—Douglas W. Robinson
*Attorney, Agent, or Firm*—Arnold, White & Durkee

[57] ABSTRACT

A drug composition for the local treatment of alopecia areata and other dermatological diseases is disclosed. The composition contains as an active ingredient an aliphatic, alkoxy or aryl substituted cyclopropenone. Diphenylcyclopropenone is a particularly preferred representative cyclopropenone useful in the context of the present invention.

16 Claims, No Drawings

DRUG COMPOSITIONS FOR LOCAL TREATMENT OF ALOPECIA AREATA

This is a continuation of copending application Ser. No. 613,253 filed May 23, 1984, which was a continuation application Ser. No. 362,474 filed Mar. 26, 1982, now both abandoned.

BACKGROUND OF THE INVENTION

This invention relates generally to pharmaceutical compositions; and in particular, it relates to drug compositions for local treatment of alopecia areata and other dermatological diseases such as viral warts.

Alopecia areata is a dermatogical condition of unknown etiology. The disease is manifested as circumscribed, noninflamed areas of baldness on the scalp, eyebrows and bearded areas of the face. Severe forms of the disease are called alopecia totalis or alopecia universalis.

In the past, treatment of alopecia areata has involved the injection of corticosteriods, namely triamcinolone acetonide suspension, into the patches of dermatologic involvement. For more progressive disease states, the resort to systemic corticosteroid therapy has been made. For the most part, however, the above listed treatments are not warranted because of the serious side effects of corticosteroids as well as from a cost stand point unless there is serious emotional or economic impact on the patient as a result of the disease.

Accordingly, there is a need for a simple, inexpensive, reliable treatment for alopecia areata and other dermatological conditions.

SUMMARY OF THE INVENTION

This invention provides a composition for the local or topical treatment of alopecia areata and other dermatological diseases. The composition contains as an active ingredient a substituted cyclopropenone with the general formula:

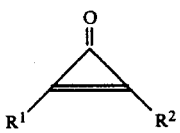

wherein the groups $R^1$ and $R^2$, which may be the same or different, represent alkyl groups with 1 to 18, especially 12 to 16 carbon atoms; alkylene groups with 3 to 18, especially 12 to 16 carbon atoms, and which may have 1, 2 or 3 conjugated or isolated C=C bonds; alkoxy groups with 1 to 4 carbon atoms in the alkyl residue; or aromatic groups such as phenyl or naphthyl, which may optionally contain halo, alkyl, monoalkylamino, dialkylamino or alkoxy groups or several of these groups as substituents. A preferred embodiment of the invention includes diphenylcyclopropenone as the active ingredient effective to treat alopecia areata and other disorders of the skin.

DETAILED DESCRIPTION OF THE INVENTION

The medicinal compositions of this invention effective for the local topical treatment of alopecia areata and other dermatologic diseases include as an active ingredient an aliphatic, alkoxy, or aryl substituted cyclopropenone of the general formula:

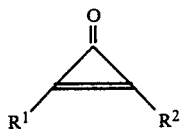

wherein the $R^1$ and $R^2$ substituent groups may be the same or different.

The substituted aliphatic groups for $R^1$ or $R^2$ can be either alkyl or alkenyl groups.

The alkyl groups as $R^1$ or $R^2$ substituents in accordance with the general formula stand for methyl, ethyl, propyl, butyl or pentyl, for example. The preferred groups are those with 12 to 16 carbons having the empirical formulas $C_{12}H_{25}$, $C_{13}H_{27}$, $C_{14}H_{29}$, $C_{15}H_{31}$ and $C_{16}H_{33}$.

The cyclopropenone with the general formula given above also contain as substituents alkylene groups with 3 to 18 carbons, especially 12 to 16 carbons, which have 1, 2 or 3 conjugated or isolated double bonds. Preferred substitutents include those in the following formulas:

$$-(CH_2)_7CH=CH(CH_2)_5CH_3$$

$$-(CH_2)_7CH=CHCH_2CH=CH(CH_2)_2CH_3$$

$$-(CH_2)_7CH=CHCH_2CH=CHCH=CHCH_3$$

$$-(CH_2)_7CH=CHCH_2CH=CHCH_2CH=CH_2$$

Of the alkyl and alkenyl groups as substituents for the cyclopropenone, linear (i.e., unbranched) groups are preferred.

Of the alkoxy groups intended as substitutents, methoxy, ethoxy, propoxy and butoxy are preferred.

The substituents $R^1$ and $R^2$ can also stand for phenyl or naphthyl, which may in turn contain as substituents halogen, alkyl, manoalkylamino, dialkylamino and/or alkoxy groups or several of these groups. Halogen here indicates in particular fluorine, chlorine, and bromine. Alkyl and alkoxy here refer in particular to groups with 1 to 4 carbons.

According to a preferred version of this invention, the drug contains diphenylcyclopropenone as the active ingredient.

The groups $R^1$ and $R^2$ may also be different. An example of this case is 1-phenyl-2-methoxycyclopropenone.

The substituted cyclopropenones employed in the present invention are known compounds which have been described in prior publications. Their preparation is well within the skill of the art. In fact, some of the preferred active cyclopropenones described herein are commercially available through chemical indices and catalogues. Heretofore, however, there has been no suggestion that the cyclopropenones described herein are useful in the topical treatment of alopecia areata and other skin diseases.

The drug composition according to this invention may contain the usual pharmaceutical vehicles and/or diluents. For example, the composition can be used in the form of a solution, especially having the cyclopropenone compound dissolved in acetone. The active ingredient may also be administered in the usual cream, or ointment formulations or together with film-forming substances.

The concentration of active ingredient of the drug composition according to this invention depends on the specific sensitization of the patient, and may vary between $10^{-5}$ and 6 wt%, with 0.01 to 3 wt% being a preferred concentration range.

The therapuetic use of the drug according to this invention in treatment of alopecia areata involves coating or contacting the diseased areas of skin with a thin layer of the drug composition about once a week. An effective dosage produces a local allergy on the treated areas of skin. After a brief period of treatment, new hair growth can be observed on the treated areas of skin.

This drug composition can also be used to treat other dermatological diseases, especially viral warts.

The above explanation is presented for the purposes of enabling those skilled in the art to practice the invention. However, upon reading this disclosure, many modifications and variations in the pharmaceutical vehicles or diluents, the dosage schedule best suited to a particular individual, or specific concentration of active ingredient for a given vehicle will become apparent to those skilled in the art. It is intended the above description not limit the scope of the invention which is defined by the following claims:

What is claimed is:

1. A method of treating alopecia areata which comprises topically applying to the affected skin area a therapeutically effective amount of a cyclopropenone with the general formula:

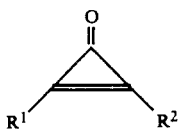

wherein $R^1$ and $R^2$, which can be identical or different groups, represent independently an alkyl group having 1 to 18 carbon atoms; an alkylene group having 3 to 18 carbon atoms and which have 1, 2 or 3 conjugated or isolated C=C bonds; an alkoxy group having 1 to 4 carbon atoms; or a phenyl or a naphthyl group which may be optionally substituted with one or more of halogen, alkyl, monoalkylamino, dialkylamino, or alkoxy groups, the alkyl or alkoxy groups thereof having 1 to 4 carbon atoms.

2. The method of claim 1 wherein the cyclopropenone compound is in combination with a pharmaceutically compatible vehicle.

3. The method of claim 2 wherein the concentration of the cyclopropenone compound is between about $10^{-5}$ and about 6 weight %.

4. The method of claim 2 wherein the concentration of the cyclopropenone compound is between 0.01 and 3 weight %.

5. The method of claim 5 wherein the pharmaceutically compatible vehicle is acetone, in which the cyclopropenone compound is dissolved.

6. The method of claim 1 wherein $R_1$ and $R_2$ of the cyclopropenone compound each represents independently a phenyl group which may be optionally substituted with one or more of halogen, alkyl, monoalkylamino, dialkylamino, or alkoxy groups, the alkyl or alkoxy groups thereof having 1 to 4 carbon atoms.

7. The method of claim 1 wherein $R_1$ and $R_2$ of the cyclopropenone compound each represents independently a phenyl group, a halogen substituted phenyl group, or an alkyl substituted phenyl group, the alkyl group having 1 to 4 carbon atoms.

8. The method of claim 7 wherein the cyclopropenone compound is diphenyl-cyclopropenone.

9. The method of claim 7 wherein the cyclopropenone compound is di-(4-chlorophenyl)-cyclopropenone.

10. The method of claim 7 wherein the cyclopropenone compound is di-(4-fluorophenyl)-cyclopropenone.

11. The method of claim 7 wherein the cyclopropenone compound is di-(4-methylphenyl)-cyclopropenone.

12. The method of claim 7 wherein the cyclopropenone compound is di-(4-tertbutyl-phenyl)-cyclopropenone.

13. The method of claim 7 wherein the cyclopropenone compound is in combination with a pharmaceutically compatible vehicle.

14. The method of claim 13 wherein the concentration of the cyclopropenone compound is between about $10^{-5}$ and about 6 weight %.

15. The method of claim 13 wherein the concentration of the cyclopropenone compound is between 0.01 and 3 weight %.

16. The method of claim 17 wherein the pharmaceutically compatible vehicle is acetone in which the cyclopropenone compound is dissolved.

* * * * *